(12) United States Patent
Green et al.

(10) Patent No.: US 10,090,146 B2
(45) Date of Patent: Oct. 2, 2018

(54) ION PROFILING WITH A SCANNING QUADRUPOLE MASS FILTER

(71) Applicant: Micromass UK Limited, Wilmslow (GB)

(72) Inventors: Martin Raymond Green, Bowdon (GB); Keith Richardson, High Peak (GB); Jason Lee Wildgoose, Stockport (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/317,035

(22) PCT Filed: Jun. 10, 2015

(86) PCT No.: PCT/GB2015/051696
§ 371 (c)(1),
(2) Date: Dec. 7, 2016

(87) PCT Pub. No.: WO2015/189605
PCT Pub. Date: Dec. 17, 2015

(65) Prior Publication Data
US 2017/0125235 A1    May 4, 2017

(30) Foreign Application Priority Data

Jun. 11, 2014 (EP) .................................... 14172021
Jun. 11, 2014 (GB) .................................. 1410427.7
Jul. 29, 2014 (GB) .................................. 1413365.6

(51) Int. Cl.
*G01N 30/26* (2006.01)
*H01J 49/26* (2006.01)
(Continued)

(52) U.S. Cl.
CPC ........ *H01J 49/4215* (2013.01); *G01N 27/622* (2013.01); *H01J 49/0036* (2013.01); *H01J 49/0045* (2013.01)

(58) Field of Classification Search
CPC ...... G01N 27/622; G01N 30/26; G01N 30/30; G01N 30/54; H01J 49/004; H01J 49/0031; H01J 49/0422; H01J 49/26
(Continued)

(56) References Cited

U.S. PATENT DOCUMENTS

| 6,177,001 | B1 * | 1/2001 | Meyer ................ G01N 27/4175 204/427 |
| 6,417,511 | B1 * | 7/2002 | Russ, IV ............... H01J 49/063 250/292 |

(Continued)

FOREIGN PATENT DOCUMENTS

| GB | 214455 | 4/1923 |
| WO | 2013/140132 | 9/2013 |
| WO | 2015/181563 | 12/2015 |

OTHER PUBLICATIONS

Henderson, S., et al.,"*ESI/Ion Trap/Ion Mobility/Time-of-Flight Mass Spectrometry for Rapid and Sensitive Analysis of Biomolecular Mixtures*", Analytical Chemistry, vol. 71, No. 2, pp. 291-301 (Jan. 1999).

*Primary Examiner* — David A Vanore
(74) *Attorney, Agent, or Firm* — Womble Bond Dickinson (US) LLP; Deborah M. Vernon; Heath T. Misley (57) ABSTRACT

A mass spectrometer is disclosed comprising an ion mobility separation device for separating ions according to their ion mobility, a first quadrupole mass filter downstream of the ion mobility separation device, a control system arranged and adapted to scan and/or step the set mass of the first quadrupole mass filter a plurality of times over a first mass to charge ratio range of <±2 amu during the elution time of an
(Continued)

2 amu scan with 1 amu transmission window. Target peak appears in the centre of the scanning window.

ion mobility peak from the ion mobility separation device, and an analyzer or ion detector downstream of the first quadrupole mass filter arranged and adapted to analyze or detect ions so as to acquire multi-dimensional ion mobility-mass to charge ratio data.

20 Claims, 3 Drawing Sheets

(51) Int. Cl.
*H01J 49/42* (2006.01)
*G01N 27/62* (2006.01)
*H01J 49/00* (2006.01)

(58) Field of Classification Search
USPC ....... 250/281, 282, 288, 287, 286, 291, 289, 250/396 R
See application file for complete search history.

(56) References Cited

U.S. PATENT DOCUMENTS

| | | | |
|---|---|---|---|
| 6,992,283 B2 * | 1/2006 | Bateman | G01N 27/622 250/281 |
| 8,153,960 B2 * | 4/2012 | Giles | H01J 49/427 250/281 |
| 8,278,622 B2 | 10/2012 | Fernandez De La Mora et al. | |
| 8,581,176 B2 | 11/2013 | Thomson et al. | |
| 8,624,179 B2 * | 1/2014 | Chen | H01J 49/0072 250/281 |
| 9,024,255 B2 * | 5/2015 | Osgood | C07B 63/00 250/281 |
| 9,190,251 B2 | 11/2015 | Green et al. | |
| 9,400,261 B2 * | 7/2016 | Black | G01N 27/624 |
| 9,523,658 B2 * | 12/2016 | Giles | G01N 27/622 |
| 9,576,779 B2 * | 2/2017 | Guna | H01J 49/0031 |
| 9,625,358 B2 * | 4/2017 | Murthy | G01N 1/2202 |
| 2002/0014586 A1 * | 2/2002 | Clemmer | G01N 27/622 250/287 |
| 2004/0245452 A1 * | 12/2004 | Bateman | G01N 27/622 250/287 |
| 2006/0071162 A1 * | 4/2006 | Crawford | H01J 49/063 250/290 |
| 2007/0034810 A1 | 2/2007 | Hoyes | |
| 2007/0164213 A1 * | 7/2007 | Javahery | H01J 49/066 250/292 |
| 2008/0111070 A1 | 5/2008 | Makarov et al. | |
| 2009/0134321 A1 | 5/2009 | Hoyes | |
| 2010/0237236 A1 | 9/2010 | Thomson et al. | |
| 2010/0282966 A1 * | 11/2010 | Schneider | G01N 27/622 250/282 |
| 2010/0301205 A1 | 12/2010 | Thomson | |
| 2011/0215235 A1 * | 9/2011 | Schoen | H01J 49/26 250/282 |
| 2013/0087701 A1 | 4/2013 | Ivosev et al. | |
| 2013/0234016 A1 | 9/2013 | Giles et al. | |
| 2014/0290340 A1 * | 10/2014 | Murthy | G01N 1/2226 73/31.07 |
| 2015/0008317 A1 * | 1/2015 | Guna | H01J 49/0031 250/283 |
| 2015/0303043 A1 * | 10/2015 | Osgood | C07B 63/00 250/282 |

* cited by examiner

For a static transmission window W the data recorded I is the sum of the intensities in the window in the dwell time d.

$$I = \sum_{t=0}^{t=d} IW_t$$

Fig. 3B

2 amu scan with 1 amu transmission window. Target peak appears in the centre of the scanning window.

Fig. 3C 2 amu scan with 1 amu transmission window. Target peak appears offset in the window may indicate a false positive result.

Fig. 3D 2 amu scan with 1 amu transmission window. Two peaks in the 1 amu window. Symmetry and peak shape indicating interference.

ION PROFILING WITH A SCANNING QUADRUPOLE MASS FILTER

CROSS-REFERENCE TO RELATED APPLICATIONS

This application represents the U.S. National Phase of International Application number PCT/GB2015/051696 entitled "Ion Profiling with a Scanning Quadrupole Mass Filter" filed 10 Jun. 2015, which claims priority from and the benefit of United Kingdom patent application No. 1410427.7 filed on 11 Jun. 2014, European patent application No. 14172021.9 filed on 11 Jun. 2014 and United Kingdom patent application No. 1413365.6 filed on 29 Jul. 2014. The entire contents of these applications are incorporated herein by reference.

FIELD OF THE PRESENT INVENTION

The present invention relates generally to mass spectrometry and in particular to methods of mass spectrometry and mass spectrometers.

BACKGROUND

It is well known to couple Time of Flight ("ToF") mass spectrometry ("MS") with ion mobility separation ("IMS") to produce multi-dimensional mass to charge ratio-ion mobility drift time-intensity data. The inherent speed of time of flight separation allows nested data sets to be acquired in which several full mass spectra are produced during the elution time of each ion mobility peak.

As ion mobility separation is somewhat orthogonal to mass separation this can increase peak capacity. For example, ions having the same mass to charge ratio (m/z) (or ions having sufficiently similar mass to charge ratios that they are partially or completely unresolved in the mass to charge ratio dimension) but with different ion mobilities may be separated in the ion mobility dimension. Processing of the data can remove mass interferences, leading to more accurate mass assignment and improved detection limits.

FIG. 6 of US 2013/234016 (Micromass) discloses a mass spectrometer having an ion mobility separation device 2 and a quadrupole filter 8.

It is desired to provide an improved method of mass spectrometry.

SUMMARY

According to an aspect there is provided a mass spectrometer comprising:
an ion mobility separation device for separating ions according to their ion mobility;
a first quadrupole mass filter arranged downstream of the ion mobility separation device;
a control system arranged and adapted to scan and/or step the set mass of the first quadrupole mass filter a plurality of times over a first mass to charge ratio range of <±2 amu during the elution time of an ion mobility peak from the ion mobility separation device; and
an analyser or ion detector arranged downstream of the first quadrupole mass filter, wherein the analyser or ion detector is arranged and adapted to analyse or detect ions so as to acquire multi-dimensional ion mobility-mass to charge ratio data.

In an embodiment multi-dimensional ion mobility-mass to charge ratio-intensity data is acquired using a quadrupole mass filter to filter ions in the mass to charge ratio dimension.

Quadrupole mass filters have not previously been used in conjunction with ion mobility separation to produce nested ion mobility-mass to charge ratio data sets. This is in large part due to their relatively slow scanning speeds of around 10000-20000 amu/sec and their low duty cycle for producing full scan mass spectra.

The Applicants have recognised a relatively simple and convenient manner in which to acquire multi-dimensional ion mobility-mass to charge ratio-intensity data. In particular, by limiting the mass to charge ratio range over which a quadrupole mass filter is scanned, it becomes possible to perform multiple scans during the elution time of an ion mobility peak, and to thereby profile individual ion mobility peaks. The approach according to various embodiments is in contrast with the arrangement disclosed in US 2013/234016 (Micromass) in which individual ion mobility peaks cannot be profiled.

Moreover, as will be described in more detail below, the techniques according to various embodiments can be used to improve mass to charge ratio measurement accuracy and/or ion mobility measurement accuracy of ions, and to improve the confidence in identification of target ions.

In an embodiment, the first mass to charge ratio range is centred at the mass to charge ratio of a target ion of interest.

In an embodiment, the control system is arranged and adapted:
to scan and/or step the set mass of the first quadrupole mass filter the plurality of times from a high mass to charge ratio to a low mass to charge ratio; or
to scan and/or step the set mass of the first quadrupole mass filter the plurality of times from a low mass to charge ratio to a high mass to charge ratio.

In an embodiment, the control system is arranged and adapted:
to scan and/or step the set mass of the first quadrupole mass filter from a high mass to charge ratio to a low mass to charge ratio and from the low mass to charge ratio to the high mass to charge ratio; or
to scan and/or step the set mass of the first quadrupole mass filter from a low mass to charge ratio to a high mass to charge ratio and from the high mass to charge ratio to the low mass to charge ratio.

In an embodiment, the mass spectrometer further comprises a fragmentation, collision or reaction device for fragmenting or reacting ions so as to produce fragment or product ions.

In an embodiment, the fragmentation, collision or reaction device is arranged downstream of the ion mobility separation device and upstream of the analyser or ion detector.

In an embodiment, the fragmentation, collision or reaction device is arranged downstream of the first quadrupole mass filter or upstream of the first quadrupole mass filter.

In an embodiment, the mass spectrometer further comprises a second quadrupole mass filter.

In an embodiment, the second quadrupole mass filter is arranged downstream of the ion mobility separation device and upstream of the analyser or ion detector.

In an embodiment, the second quadrupole mass filter is arranged downstream of the first quadrupole mass filter or upstream of the first quadrupole mass filter.

In an embodiment, the control system is arranged and adapted to keep the set mass of the second quadrupole mass filter at a constant value while the set mass of the first quadrupole mass filter is scanned and/or stepped.

In an embodiment, the second quadrupole mass filter is arranged and adapted:
to select parent ions of interest; or
to select fragment or product ions of interest.

In an embodiment, the control system is arranged and adapted to operate the first quadrupole mass filter with a resolution of around 1 amu.

In an embodiment, the control system is arranged and adapted to determine whether an ion peak in the data corresponds to a target ion based on either: (i) a determined mass to charge ratio of the ion peak relative to the first mass to charge ratio range and/or (ii) a shape of the ion peak.

In an embodiment, the control system is arranged and adapted:
to determine that the ion peak corresponds to the target ion if the determined mass to charge ratio of the ion peak is at the centre of the first mass to charge ratio range and/or corresponds with a calibrated or calculated mass to charge ratio; and/or
to determine that the ion peak does not correspond to the target ion if the determined mass to charge ratio of the ion peak is not at the centre of the first mass to charge ratio range and/or does not correspond with a calibrated or calculated mass to charge ratio.

In an embodiment, the control system is arranged and adapted to process and/or measure and/or quantify the ion peak using only data determined to correspond to the target ion.

In an embodiment, the control system is arranged and adapted to process and/or measure and/or quantify the ion peak using only data within a mass to charge ratio window centred on either: (i) a determined mass to charge ratio of the ion peak; or (ii) the centre of the first mass to charge ratio range.

In an embodiment, the mass to charge ratio window is narrower than the first mass to charge ratio range.

In an embodiment, the control system is arranged and adapted to scan and/or step the set mass of the first quadrupole mass filter the plurality of times during a dwell time for the target ion.

In an embodiment, the control system is arranged and adapted:
to determine whether an ion peak in the data comprises an ion other than a target ion based on either: (i) a determined mass to charge ratio of the ion peak relative to the first mass to charge ratio range; and/or (ii) the shape of the ion peak.

In an embodiment, the control system is arranged and adapted to determine a mass to charge ratio of an ion peak in the data.

In an embodiment, the control system is arranged and adapted to determine the mass to charge ratio of the ion peak in the data by determining a centroid of the ion peak.

According to an aspect there is provided a method of mass spectrometry comprising:
separating ions according to their ion mobility using an ion mobility separation device;
scanning and/or stepping the set mass of a first quadrupole mass filter a plurality of times over a first mass to charge ratio range of <±2 amu during the elution time of an ion mobility peak from the ion mobility separation device, wherein the first quadrupole mass filter is arranged downstream of the ion mobility separation device; and
analysing or detecting ions using an analyser or ion detector arranged downstream of the quadrupole mass filter so as to acquire multi-dimensional ion mobility-mass to charge ratio data.

According to an aspect there is provided a method of confirming the identity of an ion (or a method of mass spectrometry) comprising:
scanning and/or stepping the set mass of a first quadrupole mass filter one or more times over a first mass to charge ratio range of <±2 amu, wherein the first mass to charge ratio range is centred at the mass to charge ratio of a target ion of interest;
analysing or detecting ions so as to acquire mass spectral data; and
determining whether an ion peak in the data corresponds to the target ion of interest and/or to one or more other ions based on either: (i) the mass to charge ratio position of the ion peak within the first mass to charge ratio range; and/or (ii) the shape of the ion peak.

According to an embodiment, a method of confirming the identity of an ion peak is provided in which the set mass of a quadrupole is scanned or stepped over a range of <2 amu centred at the mass to charge ratio of a target ion of interest. It may then be determined whether an ion peak corresponds to the target ion of interest or to one or more other ions based on either: (i) the mass to charge ratio position of the ion peak within the first mass to charge ratio range; and/or (ii) the shape of the ion peak.

In an embodiment, determining whether the ion peak in the data corresponds to the target ion of interest and/or to one or more other ions based on the mass to charge ratio position of the ion peak within the first mass to charge ratio range comprises determining whether the mass to charge ratio position of the ion peak is at or close to the centre of the first mass to charge ratio range and/or corresponds to a calibrated or calculated mass to charge ratio.

In an embodiment:
if it is determined that the mass to charge ratio position of the ion peak is not at or close to the centre of the first mass to charge ratio range and/or does not corresponds to the calibrated or calculated mass to charge ratio, then it is determined that the ion peak comprises one or more other ions.

In an embodiment, the method further comprises determining the mass to charge ratio position of the ion peak within the first mass to charge ratio range by determining a centroid of the ion peak.

In an embodiment, determining whether the ion peak in the data corresponds to the target ion of interest and/or to one or more other ions based on the shape of the ion peak comprises:
determining whether the shape of the ion peak corresponds to a known or measured peak shape of the target ion of interest; and/or
determining whether the shape of the ion peak corresponds to a predicted, calculated or modelled peak shape of the target ion of interest.

In an embodiment:
if it is determined that the shape of the ion peak does not correspond to a known, measured, predicted, calculated and/or modelled peak shape, then it is determined that the ion peak comprises one or more other ions.

In an embodiment, scanning and/or stepping the set mass of the first quadrupole mass filter one or more times over the first mass to charge ratio range comprises scanning and/or stepping the set mass of the first quadrupole mass filter a plurality of times over the first mass to charge ratio range.

In an embodiment, scanning and/or stepping the set mass of the first quadrupole mass filter a plurality of times over the first mass to charge ratio range comprises:

repeatedly scanning and/or stepping the set mass of the first quadrupole mass filter from a high mass to charge ratio to a low mass to charge ratio; or repeatedly scanning and/or stepping the set mass of the first quadrupole mass filter from a low mass to charge ratio to a high mass to charge ratio.

In an embodiment, scanning and/or stepping the set mass of the first quadrupole mass filter a plurality of times over the first mass to charge ratio range comprises:

scanning and/or stepping the set mass of the first quadrupole mass filter from a high mass to charge ratio to a low mass to charge ratio and from low mass to charge ratio to the high mass to charge ratio; or scanning and/or stepping the set mass of the first quadrupole mass filter from a low mass to charge ratio to a high mass to charge ratio and from the high mass to charge ratio to the low mass to charge ratio.

In an embodiment, the method further comprises selecting or monitoring for the target ion of interest during a dwell time;

wherein scanning and/or stepping the set mass of the first quadrupole mass filter one or more times over the first mass to charge ratio range comprises scanning and/or stepping the set mass of the first quadrupole mass filter one or more times over the first mass to charge ratio range during the dwell time.

In an embodiment, the method further comprises processing and/or measuring and/or quantifying the ion peak using only data determined to correspond to the target ion.

In an embodiment, the method further comprises processing and/or measuring and/or quantifying the ion peak using only data within a second mass to charge ratio range centred at either: (i) the mass to charge ratio position of the ion peak within the first mass to charge ratio range; or (ii) the centre of the first mass to charge ratio range.

In an embodiment, the second mass to charge ratio range is narrower than the first mass to charge ratio range.

In an embodiment, the method further comprises separating ions according to their ion mobility using an ion mobility separation device.

In an embodiment, the ion mobility separation device is arranged upstream of or downstream of the first quadrupole mass filter.

In an embodiment, the method further comprises fragmenting or reacting ions so as to produce fragment or product ions using a fragmentation, collision or reaction device.

In an embodiment, the fragmentation, collision or reaction device is arranged upstream of or downstream of first quadrupole mass filter.

In an embodiment, the method further comprises:

selecting parent or precursor ions using the first quadrupole mass filter; or selecting fragment or product ions using the first quadrupole mass filter.

In an embodiment, the method further comprises filtering ions according to their mass to charge ratio using a second quadrupole mass filter.

In an embodiment, the second quadrupole mass filter is arranged upstream of or downstream of the first quadrupole mass filter.

In an embodiment, the method further comprises maintaining the set mass of the second quadrupole mass filter at a constant mass to charge ratio value while scanning and/or stepping the set mass of the first quadrupole mass filter.

In an embodiment, the method further comprises scanning and/or stepping the set mass of the second quadrupole mass filter one or more times over a third mass to charge ratio range while scanning and/or stepping the set mass of the first quadrupole mass filter.

In an embodiment:

the third mass to charge ratio range is $<\pm 2$ amu; and/or the third mass to charge ratio range is centred at the mass to charge ratio of a target ion of interest.

In an embodiment, the method further comprises:

scanning and/or stepping the set mass of the second quadrupole mass filter a single time over the third mass to charge ratio range while scanning and/or stepping the set mass of the first quadrupole mass filter a plurality of times over the first mass to charge ratio range; or scanning and/or stepping the set mass of the second quadrupole mass filter a plurality of times over the third mass to charge ratio range while scanning and/or stepping the set mass of the first quadrupole mass filter a single time over the first mass to charge ratio range.

In an embodiment, the method further comprises:

selecting parent or precursor ions using the first quadrupole mass filter and selecting fragment or product ions using the second quadrupole mass filter; or selecting fragment or product ions using the first quadrupole mass filter and selecting parent or precursor ions using the second quadrupole mass filter.

According to an aspect there is provided a mass spectrometer comprising:

a first quadrupole mass filter for filtering ions according to their mass to charge ratio;

an analyser or ion detector; and a control system arranged and adapted:

to scan and/or step the set mass of the first quadrupole mass filter one or more times over a first mass to charge ratio range of $<\pm 2$ amu, wherein the first mass to charge ratio range is centred at the mass to charge ratio of a target ion of interest;

to cause ions to be analysed or detected by the analyser or ion detector so as to acquire mass spectral data; and to determine whether an ion peak in the data corresponds to the target ion of interest and/or to one or more other ions based on either: (i) the mass to charge ratio position of the ion peak within the first mass to charge ratio range; and/or (ii) the shape of the ion peak.

According to an aspect there is provided a method of confirming the identity of an ion (or a method of mass spectrometry) comprising:

providing a first device for filtering ions according to a first physico-chemical property;

scanning and/or stepping a filtering characteristic of the first device one or more times over a first range of the first physico-chemical property, wherein the first range is centred at a value of the first physico-chemical property corresponding to a target ion of interest;

analysing or detecting ions so as to acquire mass spectral data; and determining whether an ion peak in the data corresponds to the target ion of interest and/or to one or more other ions based on either: (i) the position of the ion peak within the first range; and/or (ii) the shape of the ion peak.

In an embodiment, the first device comprises:

(i) a quadrupole mass filter for filtering ions according to their mass to charge ratio; (ii) an ion mobility filter device for filtering ions according to their ion mobility; (iii) an ion trap for filtering ions according to their mass to charge ratio; (iv) a magnetic sector mass spectrometer for filtering ions according to their mass to charge ratio; or (v) a Differential Mobility Spectrometry (DMS) or high-Field Asymmetric-waveform Ion Mobility Spectrometry (FAIMS) filtering device for filtering ions according to their rate of change of ion mobility with electric field strength.

According to an aspect there is provided a mass spectrometer comprising:

a first device for filtering ions according to a first physico-chemical property;

an analyser or ion detector; and a control system arranged and adapted:

to scan and/or step a filtering characteristic of the first device one or more times over a first range of the first physico-chemical property, wherein the first range is centred at a value of the first physico-chemical property corresponding to a target ion of interest;

to cause ions to be analysed or detected by the analyser or ion detector so as to acquire mass spectral data; and to determine whether an ion peak in the data corresponds to the target ion of interest and/or to one or more other ions based on either: (i) the position of the ion peak within the first range; and/or (ii) the shape of the ion peak.

According to an aspect there is provided a method of confirming the identity of an ion (or a method of mass spectrometry) comprising:

scanning and/or stepping the set mass of a quadrupole mass filter one or more times over a mass to charge ratio range so as to filter ions according to their mass to charge ratio, wherein the mass to charge ratio range is centred at the mass to charge ratio of a target ion;

analysing or detecting the ions so as to acquire mass spectral data;

determining whether an ion peak in the data corresponds to the target ion based on either: (i) a determined mass to charge ratio of the ion peak relative to the mass to charge ratio range and/or (ii) a shape of the ion peak.

In an embodiment, if the determined mass to charge ratio of the ion peak is at the centre of the mass to charge ratio range, then the ion peak is determined to correspond to the target ion; and if the determined mass to charge ratio of the ion peak is not at the centre of the mass to charge ratio range, then the ion peak is determined not to correspond to the target ion.

In an embodiment, the method further comprises processing and/or measuring and/or quantifying the ion peak using only data determined to correspond to the target ion.

In an embodiment, the method further comprises processing and/or measuring and/or quantifying the ion peak using only data within a mass to charge ratio window centred on either (i) a determined mass to charge ratio of the ion peak or (ii) the centre of the mass to charge ratio range.

In an embodiment, the mass to charge ratio window is narrower than the mass to charge ratio range over which the quadrupole mass filter is scanned and/or stepped.

In an embodiment, the method further comprises scanning and/or stepping the set mass of the quadrupole mass filter one or more times during a dwell time for the target ion.

In an embodiment, the method further comprises:

determining whether an ion peak in the data comprises ions other than a target ion based on either: (i) a determined mass to charge ratio of the ion peak relative to the mass to charge ratio range and/or (ii) the shape of the ion peak.

In an embodiment, scanning and/or stepping the set mass of the quadrupole mass filter one or more times comprises scanning and/or stepping the set mass of the quadrupole mass filter a plurality of times.

In an embodiment, scanning and/or stepping the set mass of the quadrupole mass filter a plurality of times comprises repeatedly scanning and/or stepping the set mass of the quadrupole mass filter over the same mass to charge ratio range.

In an embodiment, repeatedly scanning and/or stepping the set mass of the quadrupole mass filter over the same mass to charge ratio range comprises:

repeatedly scanning and/or stepping the set mass of the quadrupole mass filter from a high mass to charge ratio to a low mass to charge ratio; or repeatedly scanning and/or stepping the set mass of the quadrupole mass filter from a low mass to charge ratio to a high mass to charge ratio.

In an embodiment, repeatedly scanning and/or stepping the set mass of the quadrupole mass filter over the same mass to charge ratio range comprises:

scanning and/or stepping the set mass of the quadrupole mass filter from a high mass to charge ratio to a low mass to charge ratio and from the low mass to charge ratio to the high mass to charge ratio; or scanning and/or stepping the set mass of the quadrupole mass filter from a low mass to charge ratio to a high mass to charge ratio and from the high mass to charge ratio to the low mass to charge ratio.

In an embodiment, the mass to charge ratio range is $<\pm 2$ amu.

In an embodiment, the method further comprises determining a mass to charge ratio of an ion peak in the data.

In an embodiment, determining the mass to charge ratio of the ion peak in the data comprises determining a centroid of the ion peak.

According to an aspect there is provided a mass spectrometer comprising:

a quadrupole mass filter for filtering ions according to their mass to charge ratio;

an analyser or ion detector; and a control system arranged and adapted:

to scan and/or step the set mass of the quadrupole mass filter one or more times over a mass to charge ratio range so as to filter ions according to their mass to charge ratio, wherein the mass to charge ratio range is centred at the mass to charge ratio of a target ion;

to cause the ions to be analysed or detected by the analyser or ion detector so as to acquire mass spectral data; and to determine whether an ion peak in the data corresponds to the target ion based on either: (i) a determined mass to charge ratio of the ion peak relative to the mass to charge ratio range and/or (ii) a shape of the ion peak.

According to an aspect there is provided a method of confirming the identity of an ion (or a method of mass spectrometry) comprising:

providing a first device for filtering ions according to a first physico-chemical property;

scanning and/or stepping a filtering characteristic of the first device one or more times over a first range of the first physico-chemical property so as to filter ions according the first physico-chemical property, wherein the first range is centred at a value of the first physico-chemical property corresponding to a target ion;

analysing or detecting the ions so as to acquire mass spectral data;

determining whether an ion peak in the data corresponds to the target ion based on either: (i) a determined value of the first physico-chemical property of the ion peak relative to the first range and/or (ii) a shape of the ion peak.

In an embodiment, the first device comprises: (i) a quadrupole mass filter for filtering ions according to their mass to charge ratio; (ii) an ion mobility filter device for filtering ions according to their ion mobility; (iii) an ion trap for filtering ions according to their mass to charge ratio; (iv) a magnetic sector mass spectrometer for filtering ions according to their mass to charge ratio; or (v) a Differential Mobility Spectrometry (DMS) or high-Field Asymmetric-waveform Ion Mobility Spectrometry (FAIMS) filtering device for filtering ions according to their rate of change of ion mobility with electric field strength.

According to an aspect there is provided a mass spectrometer comprising:

a first device for filtering ions according to a first physico-chemical property;

an analyser or ion detector; and a control system arranged and adapted:

to scan and/or step a filtering characteristic of the first device one or more times over a first range of the first physico-chemical property so as to filter ions according the first physico-chemical property, wherein the first range is centred at a value of the first physico-chemical property corresponding to a target ion;

to cause the ions to be analysed or detected by the analyser or ion detector so as to acquire mass spectral data; and to determine whether an ion peak in the data corresponds to the target ion based on either: (i) a determined value of the first physico-chemical property of the ion peak relative to the first range and/or (ii) a shape of the ion peak.

According to an aspect there is provided a method of mass spectrometry comprising repeatedly scanning the set mass of a quadrupole mass filter over a mass to charge ratio range of <±2 amu.

According to an aspect there is provided a mass spectrometer comprising:

a quadrupole mass filter; and a control system arranged and adapted to repeatedly scan the set mass of the quadrupole mass filter over a mass to charge ratio range of <±2 amu.

According to an aspect there is provided a method mass spectrometry comprising:

(a) providing at least one quadrupole mass filter;

(b) providing at least one ion mobility separation device up-stream of the mass filter;

(c) scanning and/or stepping the set mass of the quadrupole mass filter one or more times over a narrow mass to charge ratio (m/z) range during the elution time of an ion mobility peak; and (d) processing the resultant mass to charge ratio-ion mobility two-dimensional data to improve confidence in target identification.

In an embodiment, the quadrupole scan range is <±2 amu.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infra-red radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms;

(v) caesium vapour or atoms; (vi) francium vapour or atoms; (vii) 060 vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenan-threne; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments will now be described, by way of example only, and with reference to the accompanying drawings in which.

DETAILED DESCRIPTION

According to an embodiment at least one quadrupole mass filter is provided and at least one ion mobility separation device is provided upstream of the mass filter. The set mass of the quadrupole mass filter may be scanned and/or stepped one or more times over a narrow mass to charge ratio range e.g. during the elution time of an ion mobility peak. The resultant multi-dimensional mass to charge ratio-ion mobility data may then be processed to improve confidence in target identification.

The quadrupole scan range may be over a mass to charge ratio range of $<\pm 2$ amu.

The set mass value of the quadrupole mass filter may be operated in resolving mode and may be scanned over a sufficiently narrow mass to charge ratio range that multiple scans may be performed during the elution time of an ion mobility peak. The resultant multi-dimensional ion mobility-mass to charge ratio data may be processed to improve the mass to charge ratio measurement accuracy and/or mobility measurement accuracy, and/or to improve the confidence in the detection of target ions and/or to improve the chromatographic signal to noise ratio.

Figure 1:
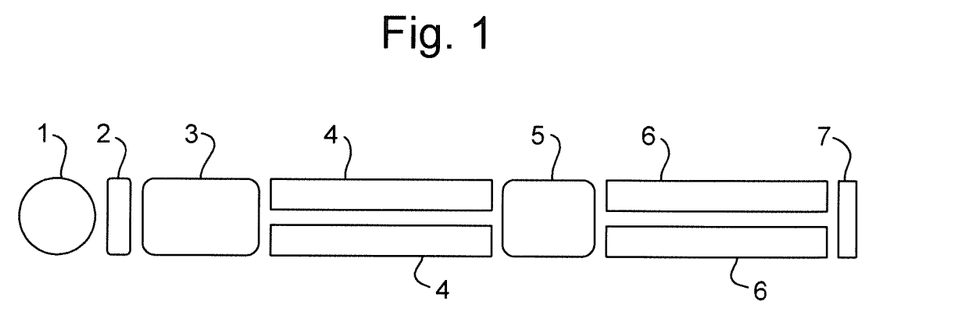
FIG. 1 shows a schematic diagram of a mass spectrometer that may be operated in accordance with an embodiment.

FIG. 1 shows an ion mobility tandem quadrupole that may be operated in accordance with an embodiment. Other arrangements may be provided and operated in accordance with other embodiments. For example, the ion mobility separation device and the quadrupole mass filter may be combined in other geometries, for example including other mass analysers such as a time of flight mass analyser.

In FIG. 1, two quadrupole mass filters 4, 6 are located downstream of an ion mobility separation device 3. Ions produced in ion source 1 are may be trapped in trapping region 2 before being released into the ion mobility separation device 3. These ions may then be selected according to their mass to charge ratio using first quadrupole mass filter (Q1) 4, and dissociated (fragmented or reacted) into product or fragment ions in reaction/collision cell 5. Product ions may be further selected according to their mass to charge ratio by second quadrupole mass filter (Q2) 6, may be before being directed to and detected by detector 7.

A typical ion mobility peak has a full width at half maximum (FWHM) of around 1 ms. For a quadrupole mass filter with a typical maximum scanning rate of 10,000 amu/sec, a 2 amu wide scan with a quadrupole resolution of 1 amu may be accomplished in 200 μs.

In embodiments where the set mass of the quadrupole is scanned multiple times, e.g. when scanning the quadrupole multiple times during the elution time of an ion mobility peak, it is desirable to minimize the inter-scan delay time required to set the quadrupole back to the starting mass to charge ratio of the scan.

To reduce or eliminate any inter-scan delay time, at the end of each narrow mass to charge ratio scan, the direction of the scan may be reversed for the subsequent scan. For example, the quadrupole may be scanned from high to low mass to charge ratio and then from low to high mass to charge ratio on consecutive scans. The data acquisition system may be configured to compensate for this reversal of scan direction, either in real time or in post processing. The quadrupole may be scanned, e.g., sinusoidally or in a saw tooth manner.

Using this method, an inter-scan period of <50 μs can be achieved, giving a total cycle time of 200-250 μs.

This method has the advantage of minimizing spectral skew due to the rapid changes in the composition of the eluting ion population during ion mobility separation.

The acquisition of mass spectral data may be continuous with no inter-scan period, or a short inter-scan period may be used to allow the data to be stored or transferred to memory. In one embodiment, the time at which the scan direction reversal occurs is "tagged" within the data.

The embodiment allows up 8 mass to charge ratio spectra to be recorded across a 1 ms (FWHM) ion mobility peak, with a duty cycle of 80%. For a 2 amu scan, the transmission relative to a static quadrupole transmission window is 50%. The overall relative sensitivity compared to a static transmission window is 40-50%.

As the ion mobility separation is orthogonal to the mass to charge ratio separation, interfering ions (e.g. precursor or parent ions) having similar or identical mass to charge ratio values may advantageously be separated according to their ion mobility.

Figure 2:
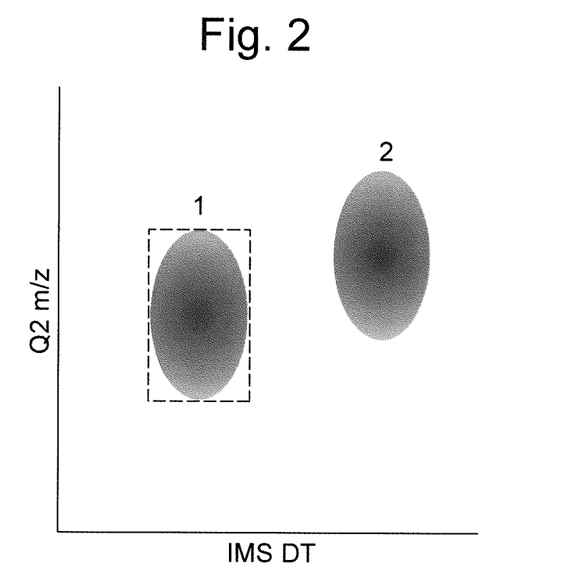
FIG. 2 shows theoretical data that may be acquired in accordance with an embodiment.

FIG. 2 shows a theoretical two-dimensional mass to charge ratio-ion mobility drift time (DT) plot resulting from an embodiment. This example data may be acquired, for example, by operating the first quadrupole (Q1) 4 of the ion mobility tandem quadrupole of FIG. 1 in a static mode in which ions within a fixed mass to charge ratio window are transmitted. The second quadrupole (Q2) 6 is scanned multiple times to profile the ion mobility separation of ions selected by the first quadrupole (Q1) 4.

In the example data shown in FIG. 2, two well resolved ion mobility peaks at drift times corresponding to precursor ions within the mass to charge ratio window of the first quadrupole (Q1) 4 are present. The mass to charge ratio scan of the second quadrupole (Q2) 6 shows that these two precursor ions give rise to two fragment ions having slightly different mass to charge ratio values, namely peaks 1 and 2.

In the example data of FIG. 2, peak 1 is in the centre of the mass to charge ratio window of the second quadrupole (Q2) 6 and would therefore (based on the mass calibration) be expected to correspond to the presence of the target ion (analyte). To add extra confidence to this identification, the drift time (or collision cross section) may be also determined and compared with the value expected for the target analyte.

In the example data of FIG. 2, peak 2 is offset from the centre of the mass to charge ratio window of the second quadrupole (Q2) 6, and is therefore unlikely to be the target ion. Again, the measured drift time may be used to improve confidence in the identification. In the embodiment, the area of one or more of the peaks and their mass to charge ratio centroids are measured. Advantageously, the area and mass centroid of each peak (e.g. peak 1) may be measured without interference from the other peaks (e.g. peak 2), thereby improving the accuracy of the quantitative results, improving the confidence in identification, and reducing false positives.

In addition, reconstructed chromatograms may be generated using only the intensity data within a defined mass to charge ratio-ion mobility drift time region associated with the target ion. In the example of FIG. 2, this region is indicated by the rectangle surrounding peak 1.

The embodiment generates higher accuracy mass to charge ratio data and drift time information, which are may be used to confirm the presence of, and to quantify a target ion.

In various other embodiments, the ion mobility separation device 3 may be situated between the first quadrupole (Q1) 4 and the second quadrupole (Q2) 6 and either the first quadrupole (Q1) 4 and/or the second quadrupole (Q2) 6 may be scanned to produce one or more nested acquisitions. Alternatively, an ion mobility separation device 3 may be provided in conjunction with a single quadrupole or a quadrupole-time of flight (Q-ToF) instrument, where the quadrupole is operated in the manner as described above.

In a further embodiment, it is recognized that during multiple reaction monitoring (MRM) or Selected Ion Recording (SIR) analysis (i.e. without ion mobility separation), a narrow quadrupole mass filter mass to charge ratio scan may also be performed, e.g. to produce a profile of an ion peak at the set mass of the quadrupole.

As is known in the art, Multiple Reaction Monitoring (MRM) is a mode of operation in which a first quadrupole mass filter is used to select target parent ions having a certain mass to charge ratio, a fragmentation, collision or reaction device is used to fragment or react the parent ions to produce product ions, and a second quadrupole mass filter is used to select target product ions having a particular mass to charge ratio.

Selected Ion Recording (SIR) is a mode of operation in which a quadrupole mass filter is used to select target ions having a particular mass to charge ratio.

In both of these modes of operation, the quadrupole mass filters are typically operated in a static mode of operation in which ions within a fixed mass to charge ratio window centred on the target mass to charge ratio are selected. A detector downstream of the quadrupole mass filters is used to detect selected ions, and an integrated intensity value is calculated. The quadrupoles may be operated so as to select certain target ions (or "transitions") during a dwell time, before begin switched to select other target ions (transitions).

In an embodiment, a narrow quadrupole mass filter (mass to charge ratio) scan is performed during multiple reaction monitoring (MRM) or Selected Ion Recording (SIR) analysis, e.g. to produce a profile of an ion peak at the set mass of the quadrupole. The centroid and/or shape of this peak may be used to assess ion peak purity and/or to determine the presence of interferences or false positives which would otherwise result in misplaced identification of a target ion.

In an embodiment, reconstructed mass chromatograms are generated from data within a restricted mass to charge ratio range, may be within the narrow mass to charge ratio scanning region. This then facilitates rejection of interference ions (i.e. from the other mass to charge ratio regions), leading to an improved signal to noise ratio compared to known quadrupole multiple reaction monitoring (MRM) and Selected Ion Recording (SIR) methods. In an embodiment, the data is used to add specificity, reduce false positives and/or improve signal to noise ratio in an automated or manual manner.

Examples of the operation of embodiments will now be described in terms of a single quadrupole system operated with a mass to charge ratio transmission window (W) of 1 amu. It will be appreciated, however, that the described techniques are applicable to other arrangements. In the following description, the edges of the transmission window (the mass instability boundaries) are assumed to be abrupt, i.e. giving an ideal flat topped transmission window.

Figure 3A:
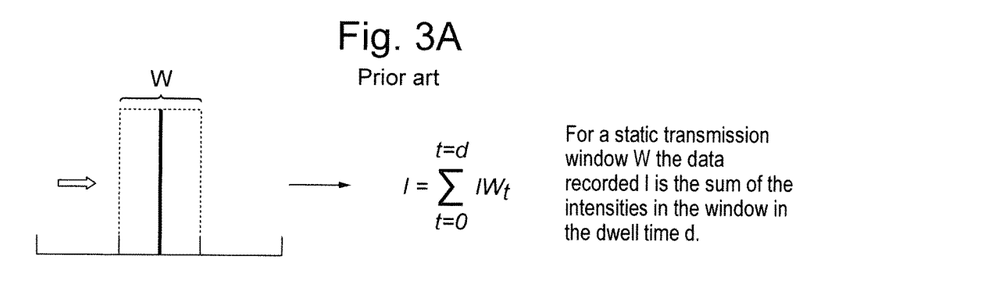
FIG. 3 illustrates the principle of operation of an embodiment.

FIG. 3A illustrates a known technique. The quadrupole is operated in a static mode in which ions within a mass to charge ratio window (W) are transmitted. The ion intensity in the window (IW) is summed over the dwell time to give a single intensity value ($I_R$). Accordingly, the data recorded in the known method is the sum of all the intensities in the window during the dwell time (d), i.e.:

$$I_R = \sum_{t=0}^{t=d} IW_t \qquad (1)$$

Figure 3B:
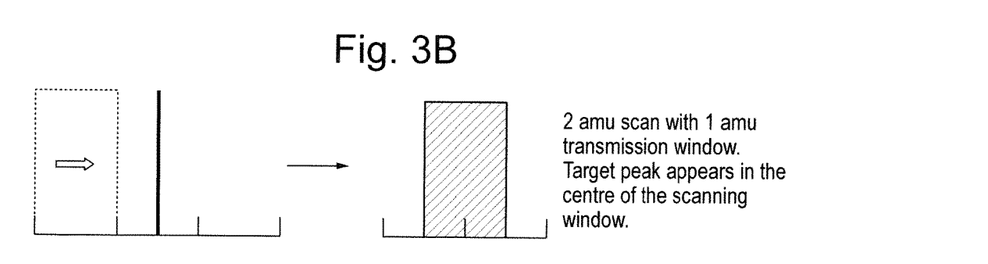

FIG. 3B illustrates an embodiment. The quadrupole is scanned over a 2 amu mass to charge ratio range during the dwell time (i.e. for each of for one or more particular target ions). The duty cycle is decreased by 50% relative to the known method, however a profile of the ion peak is recorded over a mass to charge ratio range of 2 amu centred at the set mass. In the example shown, an ion peak is present at the centre of the mass to charge ratio transmission range. The resultant recorded ion profile is centred in the transmission range.

Figure 3C:
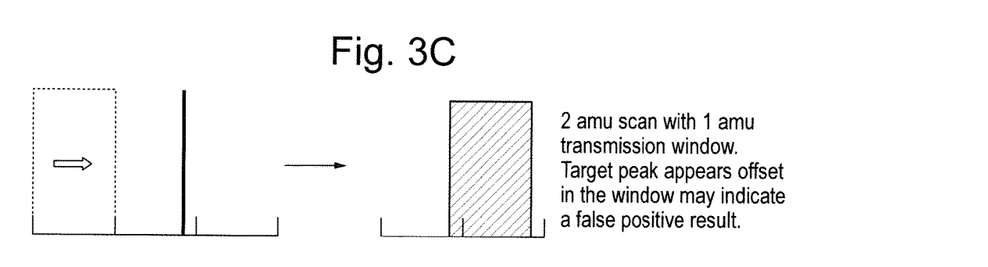

FIG. 3C further illustrates an embodiment. Again, a 2 amu wide mass to charge ratio scan is performed. In the example shown, an ion peak is present within the mass to charge ratio range of the scan, but not at its centre. The resultant recorded ion profile is offset from the centre of the range.

A centroid may be performed on this profile to produce a more accurate measure of the mass to charge ratio of the ion. In addition, with knowledge of the initial mass calibration and statistical precision, any deviation of the centroid from the centre of the mass to charge ratio range may be used to assess the likelihood of the response being a false positive. In the known method (i.e. without the profile data), this information is not available.

Figure 3D:
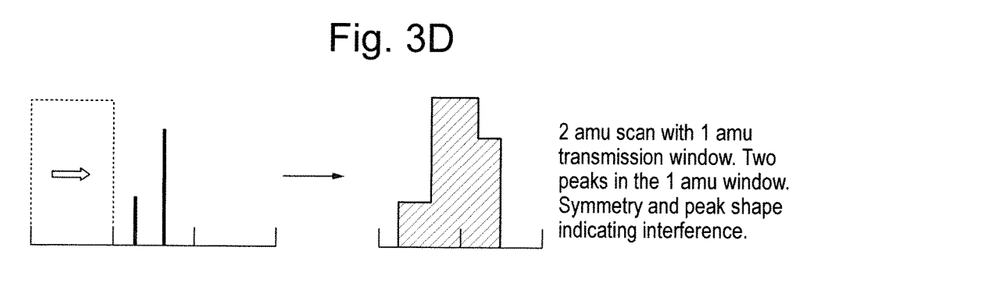

FIG. 3D further illustrates an embodiment. In the example shown, two ion peaks are present within the mass to charge ratio range. The resultant recorded ion profile has a distorted shape and a centroid offset from the centre of the range. Skew kurtosis, higher order moments, de-convolution and/or probabilistic methods may be used to assess the purity of the peak. This may be assessed with reference to known values of pure target ions, e.g. measured during calibration. Additionally or alternatively, the deviation of the ion profile relative to a model peak shape data may be assessed.

It will therefore be appreciated that the methods can be used to provide more accurate mass to charge ratio measurements and/or to assess peak purity and/or to reduce false positive identifications.

These techniques can be extended, for example, to tandem quadrupole instruments e.g. comprising a first quadrupole mass filter (Q1), a fragmentation, collision or reaction device, and a second quadrupole mass filter (Q2).

In these embodiments, if for example, the first quadrupole mass filter (Q1) is scanned during the dwell time in the manner, and the second quadrupole (Q2) is held at a static mass to charge ratio value, the mass position and purity, and mass to charge ratio centroid value of the precursor ion may be examined, i.e. in the manner discussed above. This can then aid in identifying ions.

For example, two precursor ions, e.g. having different charge states, may appear in the same isolation window of the first quadrupole (Q1) (at the same or different retention time), and may give rise to product ions with the same mass to charge ratio value (or sufficiently similar mass to charge ratio values that the ions cannot be distinguished). Using the know method, these ions will not be differentiated. In contrast, if these ions were to have different mass sufficiencies, different ion profiles would be produced using the methods. Accordingly, the profile data may advantageously be used to differentiate the two responses.

This situation may occur, for example, in the analysis of peptides. Two species may elute close to one other within a retention time window (e.g. that is being monitored for a target ion) but chromatographically resolved. In this case, it may not be possible to differentiate the target response from the interference using the known method. However, in accordance with embodiments, the signals are centroided, and mass chromatograms are may be produced over mass to charge ratio ranges within (e.g. smaller than) the initial isolation window (i.e. based on the centroid values). This can give greater specificity for the target response, leading to a reduced risk of false positives.

In an alternative embodiment, the first quadrupole (Q1) may be operated in a static mode of operation, and the second quadrupole (Q2) may be scanned. This facilitates examination of the mass position and purity of fragment or product ions. Again, if the mass sufficiency of the target product ion is different from any background signal, more specificity may be obtained. For example, halogenated target ions may be differentiated from background ions which contain no halogen atoms.

In both of these methods, the two-dimensional data may be examined after summation over the chromatographic peak, e.g. using a one- or two-dimensional peak detection algorithm.

In one embodiment, mass chromatograms are generated for (one or more or) each target ion (transition), e.g. using summed mass to charge ratio data from the entire scanning range. Chromatographic peaks are then may be detected using a two-dimensional peak detection algorithm. Once the start and end time of each peak is known, the mass to charge ratio profile data may be summed to produce a single mass to charge ratio profile for each peak in the chromatogram. This summed profile is then may be processed to produce a mass measurement and peak purity measurement.

Summing the data in this manner advantageously improves the statistical precision of the centroid mass measurement. Based on the known mass to charge ratio of the target ion and the statistical precision of the summed processed data, this mass measurement may be used to add confidence to the determination of the presence of a target ion.

In one embodiment, a three-dimensional peak detection algorithm may be applied directly to the (retention time-mass to charge ratio-intensity) data, e.g. in each MRM transition. This may be used to reduce each peak to a retention time-mass to charge ratio-intensity value. The accuracy of the mass to charge ratio values may be calculated to a higher accuracy, i.e. relative to the transmission window of the quadrupole used in the known method.

In various embodiments, the quadrupole mass filter may be scanned a single time during the dwell time for a target ion over a narrow range of, e.g., ±1 amu. For a typical dwell times of 10 ms, this requires a scanning speed of 100 amu/sec, which is well within the operational range of quadrupole mass filters.

In one embodiment, the centroid of each of the ion profiles in each of the dwell time periods (i.e. for each target ion or transition) is calculated. The chromatograms of each of the individual target ions are may be generated using mass to charge ratio windows less than the width of the mass to charge ratio transmission window of the quadrupole.

This is similar to the concept of exact mass chromatograms using a high resolution instrument. In an embodiment, the statistical precision of the measurement is calculated and used to adjust the mass to charge ratio window used to construct the chromatogram. This may be used to remove the contribution of signals which are not centred within the transmission window from the resulting chromatogram, thereby reducing false positives and improving the signal to noise ratio.

In one embodiment, to ensure the accuracy and stability of the mass calibration, a lock mass ion or reference channel/transition may be monitored, e.g. periodically, during the acquisition. In one such embodiment, a known reference standard is introduced and an SIR or MRM transition is monitored using a narrow mass to charge ratio window. The calibration may be adjusted to centre the observed peak in the transmission window. This method of ensuring mass measurement accuracy has not been applied to relatively low resolution mass filters such as quadrupole mass filters.

In another embodiment, both quadrupole mass filters in a tandem quadrupole system are scanned simultaneously. In one embodiment, the first quadrupole (Q1) is scanned once, e.g. over a 2 amu mass to charge ratio range, during the dwell time (for a particular target ion). During this time the second quadrupole (Q2) is scanned a plurality of times, such as 10 times, e.g. over a 2 amu mass to charge ratio range, to produce a nested two-dimensional data set. A 1 ms scan of the second quadrupole (Q2) over 2 amu requires a scanning speed of 2000 amu/sec, which is well within the operational scanning speed of a quadrupole mass filter.

Figure 4A:
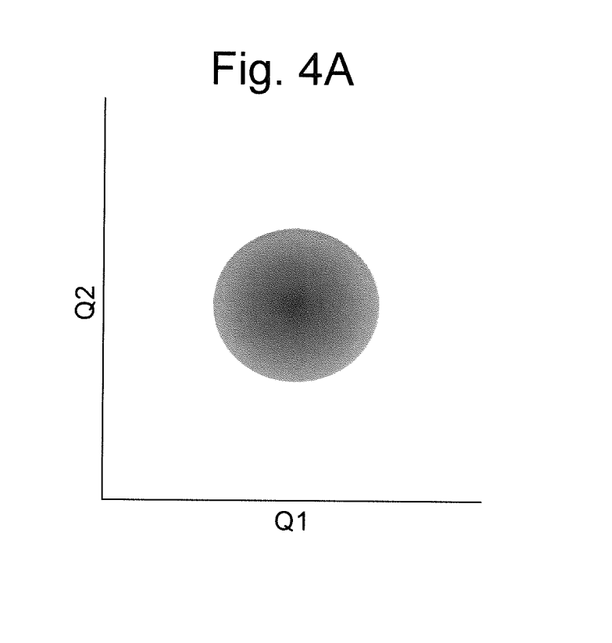
FIG. 4 shows theoretical data that may be acquired in accordance with an embodiment.
Figure 4B:
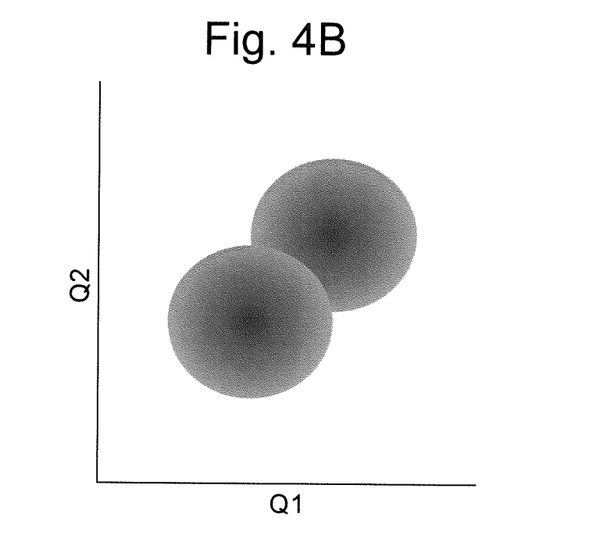

FIG. 4A shows theoretical acquired data which would be expected for a pure precursor ion and fragment ion centrally disposed in the transmission windows of the first and second quadrupoles. FIG. 4B shows theoretical acquired data in an extreme case where two precursor ions are transmitted by the first quadrupole (Q1) and two different fragment ions are present corresponding to the two precursor ions. It will be appreciated that the method of this embodiment can be used to determine the purity of ions and/or the presence of interferences. Other patterns would be expected for different interferences.

In an alternative embodiment, the second quadrupole (Q2) may be scanned once during the dwell time, and the first quadrupole (Q1) may be scanned multiple times to produce similar two-dimensional plots. Scanning both quadrupoles over a ±1 amu mass to charge ratio window results in an overall duty cycle of 25% compared with static quadrupoles.

To reduce or eliminate any inter scan delay, at the end of each narrow quadrupole mass filter scan, the direction of the scan in reversed for the subsequent scan (as described above).

In the examples discussed above, the recorded peak shapes are assumed to square. In practice, peaks have finite rise times. This non-ideal shape results from ions near edges of the quadrupole transmission window being gradually reduced in transmission, rather than being abruptly attenuated.

In an extreme example, if the transmission characteristics of the quadrupole mass filter resulted in a triangular peak shape with a 0.5 amu FWHM, a second peak could be completely resolved with no contribution to the intensity of the first peak if it were separated in mass to charge ration by at least 1 amu. If the peaks were separated by less than 1 amu, using the known method (using a static transmission window) it would not be possible to separate the two peaks (i.e. to determine if either peak were an ion of interest or an interference). In contrast, the methods may be used to distinguish such ions.

In another embodiment, the second quadrupole mass filter (Q2) is replaced with a downstream time of flight mass analyser.

As is known in the art, in tandem mass spectrometry (MS-MS) analysis using a Q-ToF, the quadrupole is typically set to transmit ions within a narrow mass to charge ratio window, selected precursor ions are fragmented or reacted to produce fragment or product ions, and a fragment or product ion spectrum is acquired using the time of flight analyser.

In an embodiment, the quadrupole is scanned over a narrow mass to charge ratio range of interest, e.g. in the manner discussed above. In this embodiment, the time of flight analyser is inherently fast enough such that several full mass spectra can be acquired during the narrow quadrupole scan over the range of interest.

Again, in this embodiment a two-dimensional plot (e.g. similar to FIG. 3B but with time of flight data in place of Q2 data) may be produced. The profile of the precursor ion peak may be interrogated for each peak in the product ion spectrum, e.g. in the manner discussed above. Fragment ions from different precursor ions are may be recognized, e.g. by their common mass profile, thereby allowing interferences in the MS-MS spectra to be recognized and accounted for, e.g. in downstream data processing.

This embodiment is of particular interest for Data Dependent Analysis (DDA) tandem mass spectrometry (MS-MS) analysis using quadrupole time of flight (Q-ToF) instruments. In known such methods, if more than one precursor ion is present within the quadrupole isolation window (chimeracy), mixed MS-MS spectra are produced which can effect compound identification. The methods can be used to address this problem.

In various embodiments, similar experiments using quadrupole mass filter and ion trap combinations, or ion mobility separation devices and ion traps, can be carried out to produce nested data sets. A narrow ion trap scan has the advantage of improving the mass resolution of the ion trap.

In various embodiments, other mass to charge ratio or ion mobility filters may be operated in a similar manner. For example, in one embodiment a narrow voltage or magnet scan may be performed in a magnetic sector mass spectrometer, e.g. during Single Ion Recording (SIR). The resultant peak profile may be examined, e.g. to determine peak purity.

In an embodiment, a narrow compensation voltage scan may be used to generate a peak profile using a Differential Mobility Spectrometry (DMS) or high-Field Asymmetric-waveform Ion Mobility Spectrometry (FAIMS) device. In one embodiment, a voltage is scanned over a narrow range to produce a ion mobility profile using a DMS device upstream of a mass spectrometer.

In various embodiments, the peak purity and/or peak position within the scanning window may be interrogated automatically in real time or in a post-acquisition processing step, e.g. to give an indication of the probability of interferences and/or false positives with the recorded data.

In various embodiments, the quadrupole may be scanned in discrete steps or in a continuous fashion. In one embodiment, a two step scan may be used. Such a scan yields higher duty cycle than a continuous scan, while still providing useful purity information via the ratio of intensities measured at the two mass to charge ratio settings. In these embodiments, centroids and/or other statistical measures of purity are may be used to analyse the data, e.g. in the manner discussed above.

In various embodiments, the methods may be selectively applied. For example, if it is known (e.g. from previous experimentation) which particular target ions are likely to suffer from interferences (and which target ions are not likely to suffer from interferences), the methods may be applied only to the former these ions, i.e. the quadrupole may be scanned for only these target ions, e.g. within a chromatographic elution time.

It will be appreciated that one embodiment provides a mode of operation of a quadrupole mass filter where nested IMS-MS or nested MS-MS profile data may be produced. This facilitates a more accurate determination of the mass to charge ratio and peak purity, and leads to a reduction is false positives, e.g. in complex matrices.

Furthermore, embodiments provide methods in by which a mass measurement may be improved and/or the peak purity of signals monitored, e.g. in targeted SIR or MRM acquisitions. This may advantageously be used to further reduce the likelihood of false positives. Improved mass measurement allows reconstruction of mass chromatograms with narrower mass to charge ratio windows based on centroided values. This can advantageously be used to reduce false positives and/or to improve the chromatographic signal to noise ratio, e.g. compared with known SIR and MRM techniques using quadrupole mass filters.

Although the present invention has been described with reference to preferred embodiments, it will be understood by those skilled in the art that various changes in form and detail may be made without departing from the scope of the present invention as set forth in the accompanying claims.

The invention claimed is:
1. A mass spectrometer comprising:
an ion mobility separation device for separating ions according to their ion mobility;

a first quadrupole mass filter arranged downstream of said ion mobility separation device;
a control system arranged and adapted to scan and/or step the set mass of said first quadrupole mass filter a plurality of times over a first mass to charge ratio range of <±2 amu during the elution time of an ion mobility peak from said ion mobility separation device; and
an analyser or ion detector arranged downstream of said first quadrupole mass filter, wherein said analyser or ion detector is arranged and adapted to analyse or detect ions so as to acquire multi-dimensional ion mobility-mass to charge ratio data.

2. A mass spectrometer as claimed in claim 1, further comprising a fragmentation, collision or reaction device for fragmenting or reacting ions so as to produce fragment or product ions;
wherein said fragmentation, collision or reaction device is arranged downstream of said ion mobility separation device and upstream of said analyser or ion detector.

3. A mass spectrometer as claimed in claim 1, further comprising a second quadrupole mass filter;
wherein said second quadrupole mass filter is arranged downstream of said ion mobility separation device and upstream of said analyser or ion detector.

4. A method of mass spectrometry comprising:
separating ions according to their ion mobility using an ion mobility separation device;
scanning and/or stepping the set mass of a first quadrupole mass filter a plurality of times over a first mass to charge ratio range of <±2 amu during the elution time of an ion mobility peak from said ion mobility separation device, wherein said first quadrupole mass filter is arranged downstream of said ion mobility separation device; and
analysing or detecting ions using an analyser or ion detector arranged downstream of said quadrupole mass filter so as to acquire multi-dimensional ion mobility-mass to charge ratio data.

5. A method as claimed in claim 4, wherein said first mass to charge ratio range is centred at the mass to charge ratio of a target ion of interest.

6. A method as claimed in claim 4, further comprising keeping the set mass of a second quadrupole mass filter arranged downstream of said ion mobility separation device and upstream of said analyser or ion detector at a constant value while the set mass of said first quadrupole mass filter is scanned and/or stepped.

7. A method as claimed in claim 4, further comprising using a second quadrupole mass filter arranged downstream of said ion mobility separation device and upstream of said analyser or ion detector:
to select parent ions of interest; or
to select fragment or product ions of interest.

8. A method as claimed in claim 4, further comprising operating said first quadrupole mass filter with a resolution of around 1 amu.

9. A method as claimed in claim 4, further comprising determining whether an ion peak in said data corresponds to a target ion based on either: (i) a determined mass to charge ratio of said ion peak relative to said first mass to charge ratio range; and/or (ii) a shape of said ion peak.

10. A method as claimed in claim 9, comprising processing and/or measuring and/or quantifying said ion peak using only data determined to correspond to said target ion.

11. A method as claimed in claim 9, comprising processing and/or measuring and/or quantifying said ion peak using only data within a mass to charge ratio window centred on either: (i) a determined mass to charge ratio of said ion peak; or (ii) the centre of said first mass to charge ratio range.

12. A method as claimed in claim 11, wherein said mass to charge ratio window is narrower than said first mass to charge ratio range.

13. A method as claimed in claim 4, further comprising:
determining whether an ion peak in said data comprises an ion other than a target ion based on either: (i) a determined mass to charge ratio of said ion peak relative to said first mass to charge ratio range; and/or (ii) the shape of said ion peak.

14. A method of confirming the identity of an ion comprising:
scanning and/or stepping the set mass of a first quadrupole mass filter one or more times over a first mass to charge ratio range of <±2 amu, wherein said first mass to charge ratio range is centred at the mass to charge ratio of a target ion of interest;
analysing or detecting ions so as to acquire mass spectral data; and
determining whether an ion peak in said data corresponds to said target ion of interest and/or to one or more other ions based on either: (i) the mass to charge ratio position of said ion peak within said first mass to charge ratio range; and/or (ii) the shape of said ion peak.

15. A method as claimed in claim 14, wherein determining whether said ion peak in said data corresponds to said target ion of interest and/or to one or more other ions based on said mass to charge ratio position of said ion peak within said first mass to charge ratio range comprises determining whether said mass to charge ratio position of said ion peak is at or close to the centre of said first mass to charge ratio range and/or corresponds to a calibrated or calculated mass to charge ratio.

16. A method as claimed in claim 15, wherein:
if it is determined that said mass to charge ratio position of said ion peak is not at or close to said centre of said first mass to charge ratio range and/or does not corresponds to said calibrated or calculated mass to charge ratio, then it is determined that said ion peak comprises one or more other ions.

17. A method as claimed in claim 14, wherein determining whether said ion peak in said data corresponds to said target ion of interest and/or to one or more other ions based on said shape of said ion peak comprises:
determining whether said shape of said ion peak corresponds to a known or measured peak shape of said target ion of interest; and/or
determining whether said shape of said ion peak corresponds to a predicted, calculated or modelled peak shape of said target ion of interest.

18. A method as claimed in claim 14, further comprising filtering ions according to their mass to charge ratio using a second quadrupole mass filter; and
maintaining the set mass of said second quadrupole mass filter at a constant mass to charge ratio value while scanning and/or stepping the set mass of said first quadrupole mass filter.

19. A method as claimed in claim 14, further comprising filtering ions according to their mass to charge ratio using a second quadrupole mass filter; and
scanning and/or stepping the set mass of said second quadrupole mass filter one or more times over a third mass to charge ratio range while scanning and/or stepping the set mass of said first quadrupole mass filter.

20. A method as claimed in claim 19, further comprising:
scanning and/or stepping the set mass of said second quadrupole mass filter a single time over said third mass to charge ratio range while scanning and/or stepping the set mass of said first quadrupole mass filter a plurality of times over said first mass to charge ratio range; or scanning and/or stepping the set mass of said second quadrupole mass filter a plurality of times over said third mass to charge ratio range while scanning and/or stepping the set mass of said first quadrupole mass filter a single time over said first mass to charge ratio range.

* * * * *